US00PP18975P2

(12) United States Plant Patent
Olesen

(10) Patent No.: US PP18,975 P2
(45) Date of Patent: Jun. 24, 2008

(54) MINIATURE ROSE PLANT NAMED 'POULMIST'

(50) Latin Name: *Rosa hybrid*
Varietal Denomination: Poulmist

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 133 days.

(21) Appl. No.: 11/388,337

(22) Filed: Mar. 23, 2006

Related U.S. Application Data

(63) Continuation of application No. 10/916,341, filed on Aug. 10, 2004, now abandoned, which is a continuation of application No. 09/655,262, filed on Sep. 5, 2000, now abandoned.

(51) Int. Cl.
*A01H 5/00* (2006.01)

(52) U.S. Cl. ..... Plt./118

(58) Field of Classification Search ..... Plt./118
See application file for complete search history.

(56) References Cited

PUBLICATIONS

UPOV–ROM GTITM, Plant Variety Database, 2007/02, GTI Jouve Retrieval Software, Citation for *Rosa* 'Poulmist' one page.*
Poulsen Roser A/S [online], [retrieved on Sep. 17, 2007. Retrieved from the Internet <http://www.poulsenroser.dk/VisStandartSide.asp?iSideID=572&emneid=6&menu=429> 3 pages.*

* cited by examiner

*Primary Examiner*—Kent Bell
*Assistant Examiner*—June Hwu

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa* hybrid.
Variety denomination: 'Poulmist'.

SUMMARY OF THE INVENTION

The present invention constitutes a new and distinct variety of miniature rose plant which originated from a controlled crossing between an unnamed seedling and 'POULjol'. The two parents were crossed and the resulting seeds were planted in a controlled environment. The new variety is named 'Poulmist'.

The new rose may be distinguished from its seed parent, an unnamed seedling, by the following characteristic:

1. The unnamed seed parent is a miniature rose variety with bi-color red and yellow flowers.

The new variety may be distinguished from its pollen parent, 'POULjol', a non-patented rose created by the same inventors, by the following combination of characteristics:

1. The pollen parent has blooms which are a more muted yellow than that of 'Poulmist's blooms.
2. The flowers of 'Poulmist' have significantly better longevity than 'POULjol'.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

The combination of qualities of this variety represents significant improvement over previously available commercial cultivars of this type and distinguishes 'Poulmist' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulmist' was selected by the inventors as a single plant from the progeny of the hybridization in May of 1997. Asexual reproduction of 'Poulmist' by cuttings and traditional budding was first done by Mogens N. Olesen in Fredensborg, Denmark, in August of 1997. This initial and other subsequent propagations conducted in controlled environments have demonstrated that the characteristics of 'Poulmist' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'Poulmist'.

Specifically illustrated in SHEET 1:

1. Flowering stem showing branching and the attachment of leaves, buds, and peduncles;
2. Flower bud, partially opened bud, and open bloom;
3. Flower petals, detached;

4. Calyx; sepals detached;
5. Bare stem and bare stem with leaf and bud;
6. Leaves.

DETAILED DESCRIPTION OF THE VARIETY

The following is a description of 'Poulmist', as observed in its growth in glasshouses in; Half Moon Bay, Calif. The observed plants were 75 days of age. Color references are made using The Royal Horticultural Society (London, England) Colour Chart, 1995, except where common terms of color are used.

For a comparison, several physical characteristics of the rose variety 'POULgelb', a miniature rose variety from the same inventor, described and illustrated in U.S. Plant Pat. No. 9,401, are compared to 'Poulmist ' in Table 1.

TABLE 1

| | 'Poulmist' | 'POULgelb' |
|---|---|---|
| Petal Color, Upper Surface: | Yellow Group 12A to 12B | Yellow Group 13C. |
| Petal Color, Lower Surface: | Yellow Group 12A to 12B | Yellow Group 13C. |
| Petalage: | Very Double: 35 to 40 petals under normal conditions. | Very Double: 30 to 40 petals under normal conditions. |

Parents: An unnamed seedling×'Pouljol'.
Classification:
*Botanical.*—*Rosa hybrid.*
*Commercial.*—Miniature.

FLOWER AND FLOWER BUD

Blooming habit: Continuous.
Flower bud:
*Size.*—Upon opening, 13 mm to 20 mm in length from base of receptacle to end of bud. Bud is 7 mm to 10 mm in diameter upon opening.
*Bud form.*—Medium; pointed ovoid.
*Bud color.*—As sepals unfold, Yellow Group 9B, Yellow Group 9B at ¼ opening.
*Sepals.*—Lower surface is Yellow-Green Group 144A. Strong foliaceous appendages on three of the five sepals. Upper surfaces of sepals moderately pubescent. Stipitate glands are present on edges of sepals. Normally 20 mm long by 6 mm wide.
*Receptacle.*—Surface: Smooth. Shape: Cup-shaped. Size: 5 mm (h)×6 mm (w). Color: Yellow-Green Group 144A.
*Peduncle.*—Surface: Smooth. Length: 50 mm to 60 mm average length. Color: Yellow-Green Group 144A. Strength: Strong.
*Borne.*—Generally with 1 to 2 buds per flowering stem.
Flower bloom:
*Fragrance.*—None.
*Duration.*—As a pot plant, flowers last from 14 to 17 days. As a cut flower 5 to 7 days.
*Size.*—Small for a 15 cm pot rose. Average flower diameter is 40 mm when open.
*Form.*—Shape of flower when viewed from the side: Upon opening, upper part: Convex. Upon opening, lower part: Convex. Open flower, upper part: Convex. Open flower, lower part: Concave.
*Petalage.*—Average range, 35 to 40 petals under normal conditions with 3 to 4 petaloids.
Color:
*Upon opening, petals.*—Outermost petals: Upper Surface: Yellow Group 12 A to 12B. Reverse Side: Yellow Group 12 A to 12B. Innermost petals: Upper Surface: Yellow Group 12 A to 12B. Reverse Side: Yellow Group 12 A to 12B.
*Upon opening, basal petal spots.*—Outermost petals: Outer Side: Yellow Group 11D. Inner Side: No petal spots observed. Innermost petals: Outer Side: Yellow Group 11D. Inner Side: No petal spots observed.
*After opening, petals.*—Outermost petals: Upper Surface: Yellow Group 11C. Reverse Side: Yellow Group 11C. Innermost petals: Upper Surface: Yellow Group 11C. Reverse Side: Yellow Group 11C.
*After opening, basal petal spots.*—None observed.
General tonality: On open flower Yellow Group 12B. No change in the general tonality at the end of the 8th day. Afterwards, general tonality is Yellow Group 11C.
Petals:
*Petal reflex.*—Double.
*Petal edge.*—Entire. Some have a point in center of margin.
*Shape.*—Round. Apex is rounded. Base is acute.
*Size.*—20 mm in length by 19 mm width.
*Petaloids.*—3 to 4. Average size is 10 mm long by 5 mm wide. Yellow 11C in color.
*Texture.*—Smooth.
*Arrangement.*—Imbricated.
Reproductive organs:
*Pollen.*—Color: Yellow Group 2A. Quantity: Limited.
*Anthers.*—Size: 1 mm to 2 mm. Color: Greyed-Yellow Group 160C. Abundance: 30 actual count.
*Filaments.*—Color: Yellow-Green Group 145C, with an intonation of Greyed-Purple Group 180B immediately below anther. Length: 3 mm.
*Stigmas.*—Slightly inferior in position relative to anthers. Color: Greyed-Green Group 193C. Abundance: 22 actual count.
*Styles.*—Color: Yellow-Green Group 145C, with intonations of Greyed-Purple Group 180B immediately below stigma. Length: 4 mm.

PLANT

Plant growth: Vigorous and compact. When grown as a 15 cm pot plant, the average height of the plant is 22 cm to 27 cm and the average width is 20 cm to 25 cm.
Stems:
*Color.*—Young wood: Yellow-Green Group 144A. Older wood: Yellow-Green Group 144A.
*Prickles.*—Incidence: Few. Size: Average length: 4 mm to 6 mm. Color: Greyed-Yellow Group 160C. Shape: Linear.
*Surface.*—Young wood: Smooth. Older wood: Smooth.
*Size.*—Length: 15 cm from flower bud to $1^{st}$ branch. Diameter: 4 mm.
Plant foliage: Normal number of leaflets on leaves in middle of the stem: 5 leaflets.
*Leaf size.*—Terminal leaflets are 30 mm (l)×16 mm (w). Compound leaves are generally 71 mm long by 47 mm wide.
*Abundance.*—Very abundant.
*Color.*—Upper Leaf Surface: Green Group 137A. Lower Leaf Surface: Green Group 137B. Juvenile foliage: Green Group 138A. Anthocyanin intonation: None observed.

Plant leaves and leaflets:

*Stipules.*—Size: 8 m to 11 mm. Color: Green Group 137A with intonations of Green Group 143C. Stipitate glands: Present on margins of stipules.

*Petiole.*—Length: 9 mm to 10 mm. Color: Yellow-Green Group 144A. Underneath: Yellow-Green Group 144A. Margins: Green Group 139A. Surface Texture: Smooth.

*Rachis.*—Color: Yellow-Green Group 144A. Underneath: Yellow-Green Group 144A. Margins: Green Group 139A. Surface Texture: Smooth.

*Leaflet.*—Edge: Serrated. Shape: Ovoid. Texture: Smooth.

Disease resistance: Average resistance to powdery and downy mildew, black spot, and *Botrytis* under normal growing conditions in Half Moon Bay, Calif.

Cold tolerance: The variety has been observed to be cold tolerant to USDA Cold Hardiness Zone 7.

It is claimed:

1. A new and distinct variety of rose plant named 'Poulmist' of the miniature rose class, illustrated and described herein as a distinct and novel rose variety due to its abundant Yellow Group 11C flowers, vigorous and compact growth, year round flowering under glasshouse conditions, suitability for production from softwood cuttings in pots, and durable flowers and foliage with an extended period of bloom.

* * * * *

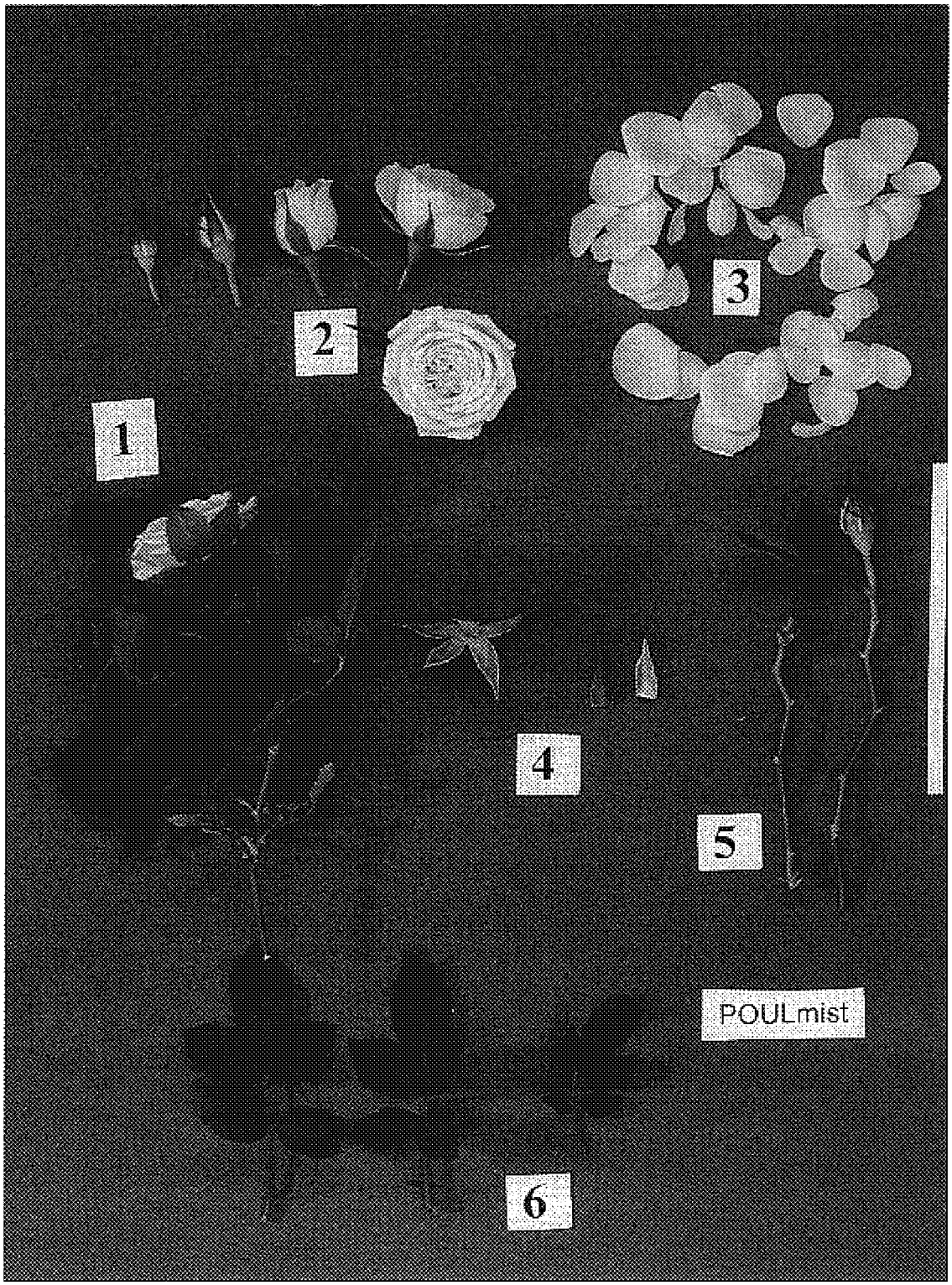
1
2
3
4
5
POULmist
6